US008349832B2

(12) United States Patent
Foley et al.

(10) Patent No.: US 8,349,832 B2
(45) Date of Patent: *Jan. 8, 2013

(54) COMPOUNDS AND COMPOSITIONS FOR TREATING CANCER

(75) Inventors: Michael Andrew Foley, Chestnut Hill, MA (US); Robert Gould, Beverly, MA (US); Peter Elliott, Marlboro, MA (US); Anna Mandinova, Newton, MA (US)

(73) Assignees: Canthera Therapeutics, Boston, MA (US); The Massachusetts General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/874,306

(22) Filed: Sep. 2, 2010

(65) Prior Publication Data

US 2011/0053938 A1    Mar. 3, 2011

Related U.S. Application Data

(60) Provisional application No. 61/275,754, filed on Sep. 2, 2009.

(51) Int. Cl.
| A61K 31/5377 | (2006.01) |
| A61K 31/4412 | (2006.01) |
| C07D 413/12 | (2006.01) |
| C07D 211/86 | (2006.01) |
| A61P 35/00 | (2006.01) |

(52) U.S. Cl. ............... 514/235.5; 514/350; 544/131; 546/298

(58) Field of Classification Search .............. None
See application file for complete search history.

(56) References Cited

U.S. PATENT DOCUMENTS

| 6,683,079 B2 | 1/2004 | Bisagni et al. |
| 6,706,021 B2 | 3/2004 | Lu et al. |
| 2005/0250768 A1 | 11/2005 | Link et al. |
| 2007/0244164 A1 | 10/2007 | Yan et al. |
| 2008/0220416 A1 | 9/2008 | Miele et al. |
| 2008/0227829 A1 | 9/2008 | Hammerstone |
| 2009/0312373 A1 | 12/2009 | Lee et al. |

FOREIGN PATENT DOCUMENTS

| WO | WO 2006/047354 A1 | 5/2006 |
| WO | WO2008112195 A1 | 9/2008 |

OTHER PUBLICATIONS

Park et al., caplus an 2008:1229445.*
Raza, et al., "Phase 1-2a multicenter dose-escalation study of ezatiostat hydrochloride liposomes for injection" J. Hematology & Oncology, 2:20, May 13, 2009; 12 total pages.
Proghost Research, "Engines of Momentum: Clinical Trial News: TELIK (TELK)" Dec. 6, 2004 1-2.
Srivastava et al., "Synthesis of diverse analogues of Oenostacin and their antibacterial activities", Biorganic & Medicinal Chemistry, vol. 15; Oct. 10, 2006, pp. 518-525.
Boll, et al., "Synthesis and Molecular Structure of Piplartine", Tetrahedron vol. 40, No. 1, pp. 171-175, (1984).
Dyer, et al., "Isolation, Synthesis and Evolutionary Ecology of Piper Amides", PI: MRM/IKJ, 117-139, 2004.
Joshi, et al., On the Structure of Piplartine and a Synthesis of Dipydropiplartine, Tetrahedron Letters No. 20, Pergamon Press, pp. 2395-2400, (1968).
Park, et al. "Antiplatelet Activities of Newly Synthesized Derivatives of Piperlongumine", Phythother.Res.22, pp. 1195-1999, (2008).
Fincher, et al. , "Inter- and Intraspecific Comparisons of Antiherbivore Defenses in Three Species of Rainforest Understory Shrubs", J Chem Ecol, vol. 34, pp. 558-574, (2008).
Negi, et al. "A Simple Regioselective Demethylation of p-Aryl Methyl Ethers Using Aluminum Chloride-Dicholoromethane System", Synthetic Communications, vol. 35:1,pp. 15-21, 2005.
Bezerra, D.P., et al; In vivo growth-inhibition of Sarcoma 180 by piplartine and piperine, two alkaloid amides from Piper; Brazilian Journal of Medical and Biological Research (2006) 39:801-807.
Bezerra et al.; Research Thesis; Estudo das Propriedades Anticancer da Piplartina; Jun. 27, 2008.

* cited by examiner

Primary Examiner — Sun Jae Loewe
(74) Attorney, Agent, or Firm — Fish & Richardson P.C.

(57) ABSTRACT

The invention relates to compounds and composition for the treatment and prevention of cancer. The invention also covers all diseases that may be treated by selective modulation of levels of reactive oxygen species in diseased cells versus normal cells. Methods for the preparation and administration of such compositions are also disclosed.

12 Claims, 6 Drawing Sheets

COMPOUNDS AND COMPOSITIONS FOR TREATING CANCER

CLAIM OF PRIORITY

This application claims priority to U.S. Provisional Application Ser. No. 61/275,754, filed Sep. 2, 2009 and entitled "COMPOUNDS AND COMPOSITIONS FOR TREATING CANCER" which is incorporated by reference in its entirety."

FIELD OF THE INVENTION

The invention relates to compounds and composition for the treatment and prevention of cancer. The invention also covers all diseases that may be treated by selective modulation of levels of reactive oxygen species in diseased cells versus normal cells. Methods for the preparation and administration of such compositions are also disclosed.

BACKGROUND OF THE INVENTION

The present invention relates to compounds and compositions for the treatment and prevention of cancer, or decreasing the intensity or duration of cancer. The invention also covers all diseases that may be treated by selective modulation of levels of reactive oxygen species in diseased cells versus normal cells.

All living aerobic cells are normally exposed to some reactive oxygen species (ROS) but if ROS levels rise, oxidative stress (OS) occurs, which results in oxygen and oxygen-derived oxidants, and in turn increases the rates of cellular damage. Cells are exposed to both endogenous and exogenous sources of ROS. At high levels, ROS can lead to impaired physiological function through cellular damage of DNA, proteins, lipids, and other macromolecules, which can lead to certain human pathologies including cancers, neurodegenerative disorders, and cardiovascular disease, as well as aging. Moreover, ROS are important in mediating apoptosis.

Selectively increasing levels of ROS in cancer cells and not normal cell may be a safe and effective method for treating cancer. FIG. 6 shows cancer therapies targeting various hallmarks of cancer.

Reducing ROS leads to treatment of neurodegenerative diseases, inflammation and for the treatment of a broad range of disorders including, neurodegenerative diseases, chronic inflammatory diseases, inflammatory bowel disease, rheumatoid arthritis, psoriasis, multiple sclerosis, endotoxin shock, osteoporosis, Alzheimer's disease, congestive heart failure and skin disease.

There remains a need for compounds which can increase ROS in cancer cells while reducing or maintaining ROS levels in normal cells.

SUMMARY OF THE INVENTION

Compounds and compositions that are useful for the treatment and prevention of cancer are provided. The present invention encompasses compounds having the following formula IA, or salts, derivatives, or mixtures thereof:

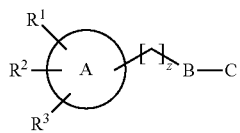

or a pharmaceutically acceptable salt or pharmaceutically acceptable derivative thereof, wherein:

Ring A is selected from the group consisting of one or more monocyclic aryl, one or more heteroaryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen, or sulfur;

each $R^1$, $R^2$, and $R^3$ is independently selected from the group consisting of hydrogen, halogen, deuterium, $CF_3$, CN, OR, SR, NRR, NRCOR, NRCONRR, $NRCO_2R$, COR, $CO_2R$, NOR, $NO_2$, CONRR, OC(O)NRR, $SO_2R$, $SO_2NRR$, $NRSO_2R$, $NRSO_2NRR$, C(O)C(O)R, or $C(O)CH_2C(O)R$, alkyl, aryl, heteroaryl and morpholino, wherein either $R^1$ and $R^2$, or $R^2$ and $R^3$ are optionally taken together to form a 4-8 membered saturated, partially unsaturated, or fully unsaturated ring having 0-3 heteroatoms independently selected from nitrogen, oxygen, or sulfur; and z is 0, 1 or 2;

each R is independently selected from hydrogen or an optionally substituted $C_1$-$C_4$ aliphatic moiety, wherein:

or alternately, two R moieties bound to the same nitrogen atom are optionally taken together with the nitrogen atom to form a 3-7 membered saturated, partially unsaturated, or fully unsaturated ring having 1-2 additional heteroatoms independently selected from nitrogen, oxygen, or sulfur;

B is selected from:

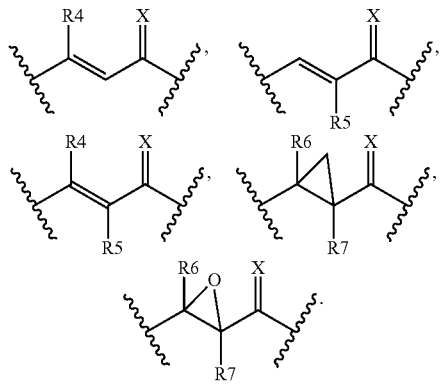

wherein

R4, R5, R6 and R7 are independently selected from a substituted or unsubstituted $C_1$ to $C_{12}$ alkyl, a substituted or unsubstituted $C_1$ to $C_{12}$ alkenyl or a substituted or unsubstituted $C_1$ to $C_{12}$ alkynyl;

X is O, S; and

C is a saturated or unsaturated heteroaryl or a saturated or unsaturated C1 to C7 heterocyclic containing one or more hetero atoms wherein the heteroatoms are independently selected from N, O or S;

or C a fused ring; and wherein any one or more H is optionally replaced by a deuterium.

The compounds of the present invention may be produced using piperlongumine as a starting material yet offer numerous advantages over piperlongumine. In the course of the experimental investigations, it was found that more than 0.25 mg/ml of piperlongumine in DMSO was precipitated out when diluted 1:10 in phosphate buffered saline or water. It was also found that piperlongumine is soluble in water at 0.1 mg/mL. The compounds of the instant invention are highly soluble in water at concentration of at least 25 mg/mL facilitating pharmaceutical preparation and delivery. Many chemotherapeutic agents transiently increase ROS levels in both cancer cells and normal cells. In contrast, the compounds of the instant invention have a large therapeutic window and do not increase ROS or cause DNA damage in normal cells. Compared to current standards such as etoposide, 5-fluorouracil, cisplatin and taxol, the drug is comparable in its effect on net cancer cell growth (melanoma, ovarian, renal, glioblastoma, drug-resistant non-small cell lung cancer cell lines) as a percent of control.

DESCRIPTION OF THE PREFERRED EMBODIMENTS

Definitions

Figure 1:
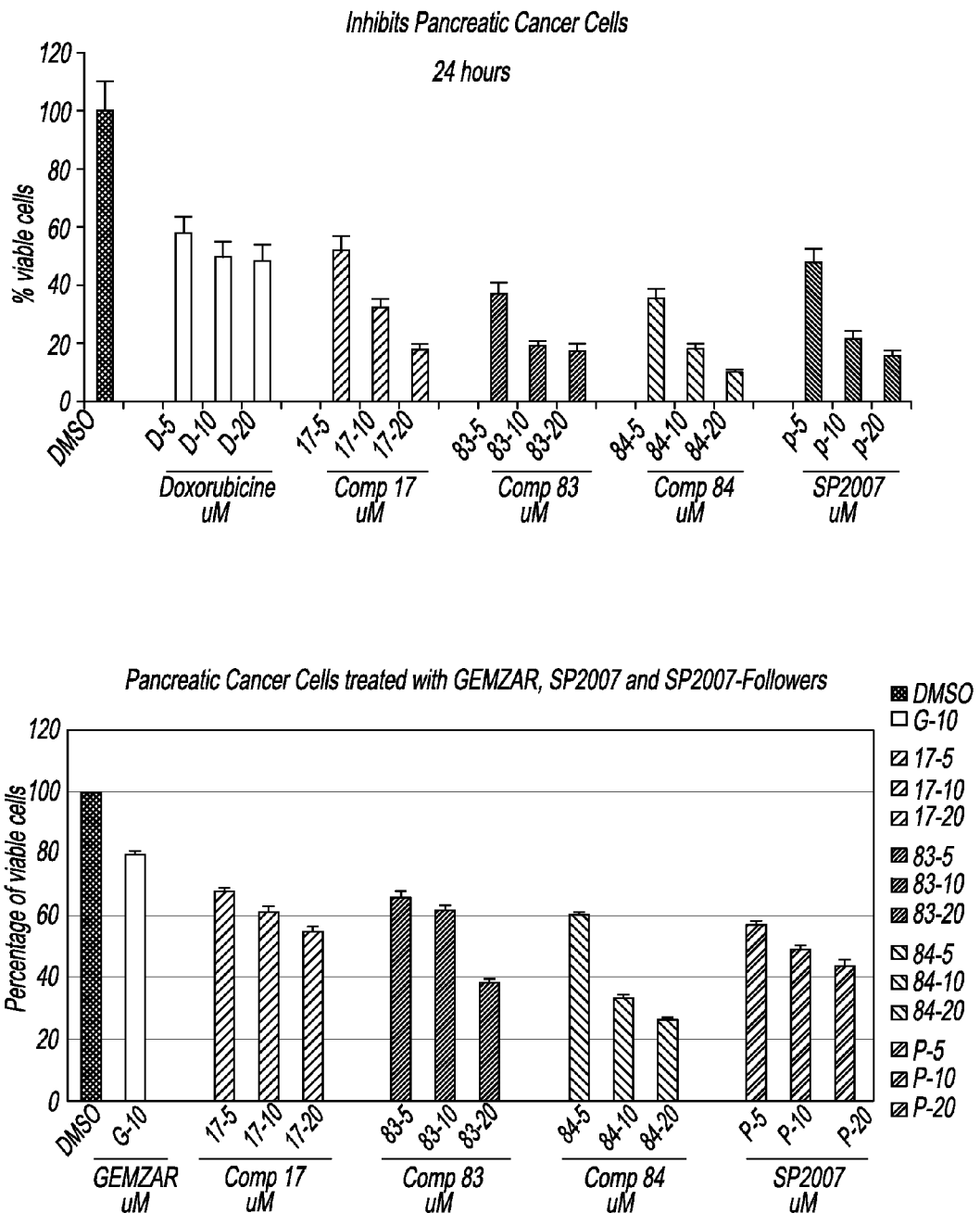
FIG. 1 shows the effect of compounds on pancreatic cells
Figure 2:
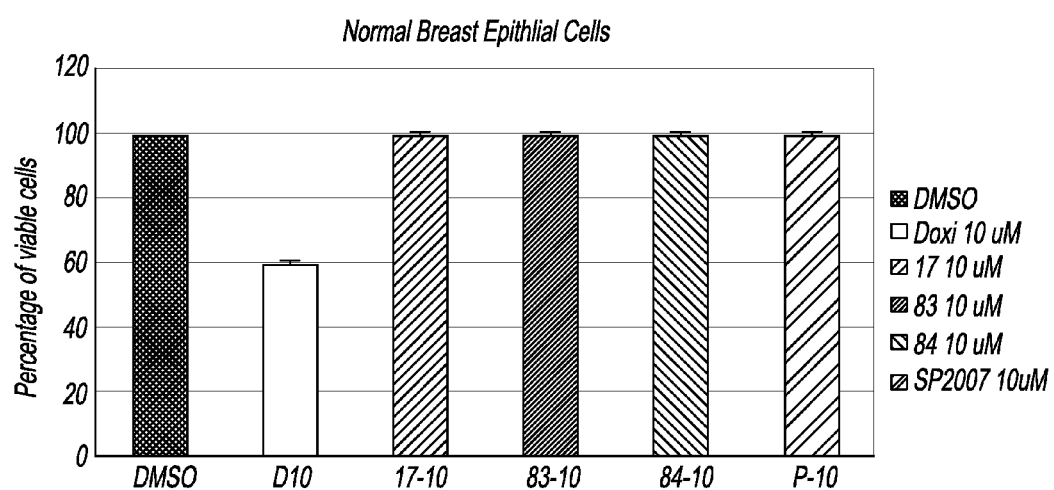
FIG. 2 shows viability of normal breast epithelium in the presence of compounds of the invention.
Figure 3:
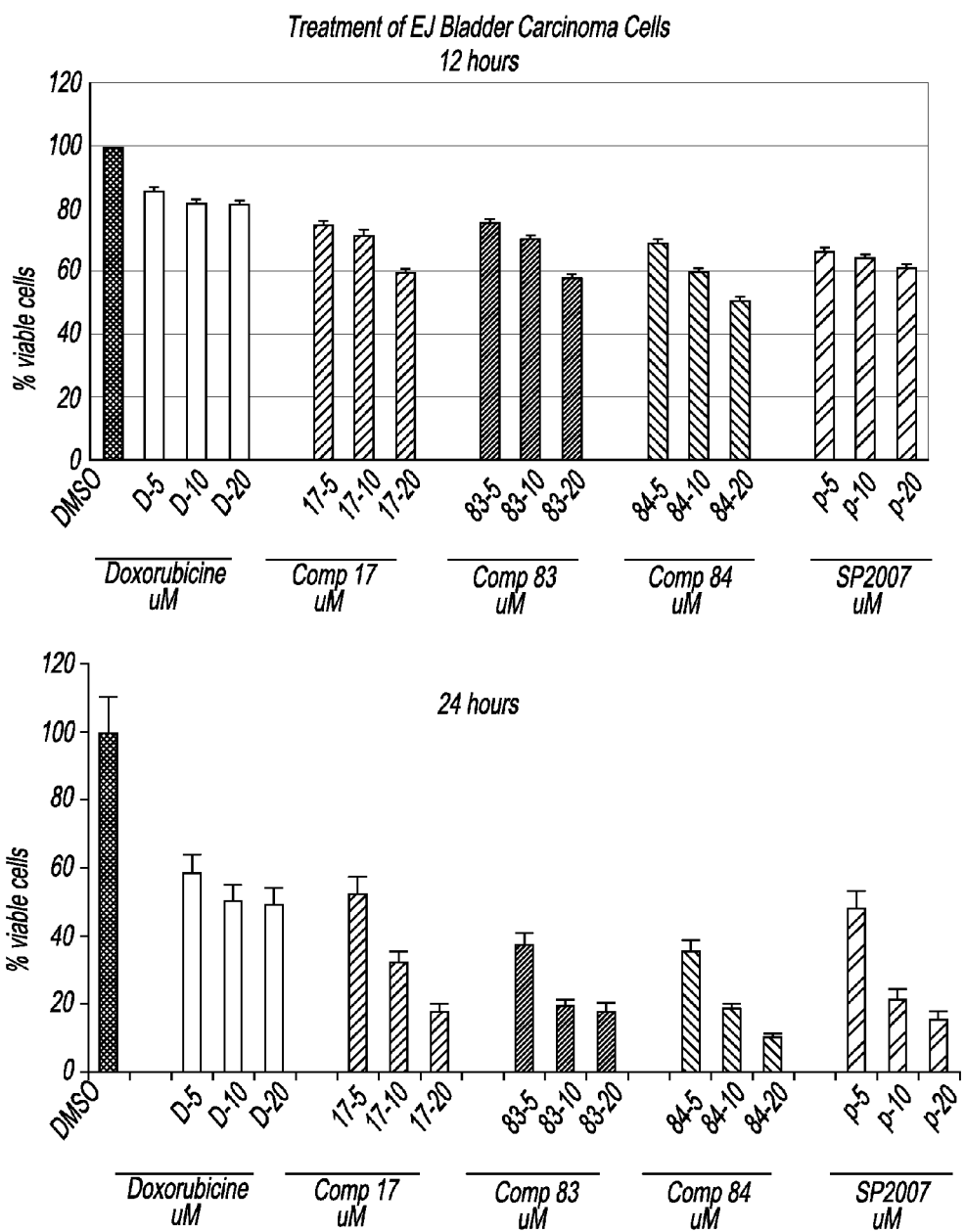
FIG. 3 shows the effect of compounds on EJ Bladder Carcinoma cells
Figure 4:
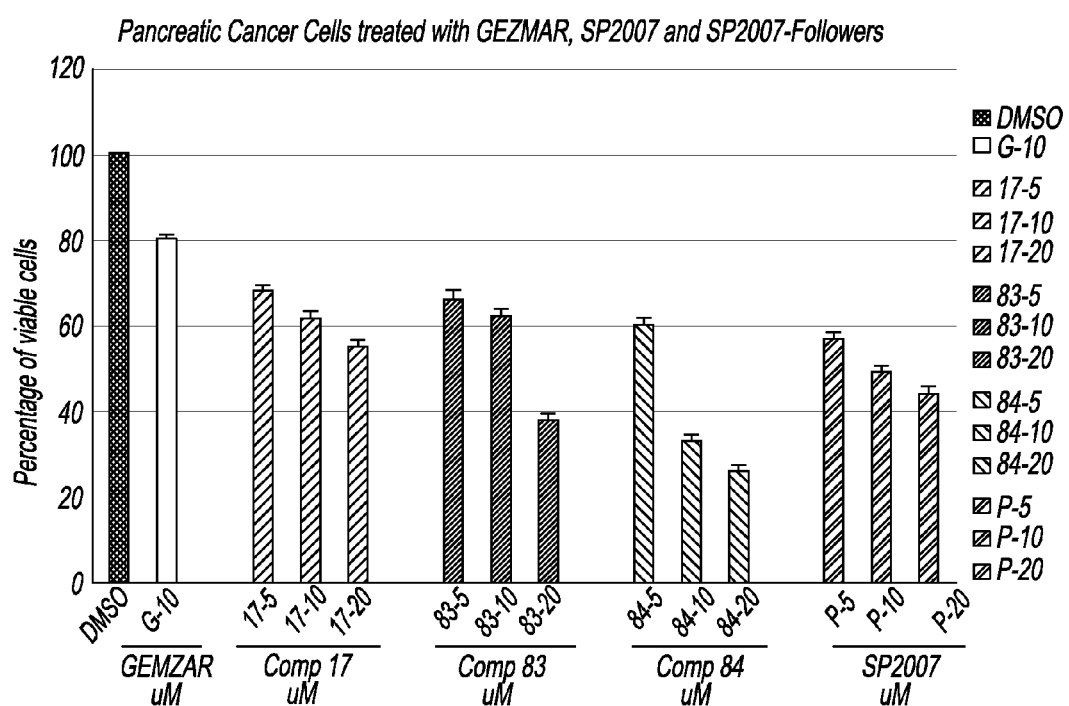
FIG. 4 shows the effect of compounds on pancreatic cells

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean a range of up to 10%, preferably up to 5%.

The terms "alkyl", "alkenyl", "alkoxy", "alkylene", "alkenylene", "alkenyl", "alkyl(arylene)", "alkynyl", and "aryl (alkylene)" include, but are not limited to, linear and branched alkyl, alkenyl, alkoxy, alkylene, alkenylene, alkyl (arylene), and aryl(alkylene) groups, respectively.

The phrase "pharmaceutically acceptable" refers to compounds or compositions that are physiologically tolerable and do not typically produce an allergic or similar untoward reaction, such as gastric upset, dizziness and the like, when administered to a mammal.

An "effective amount of compound" means the amount of compound, salt or salts, or (including its solvates, active metabolites, prodrugs, or racemates or enantiomers thereof (assuming the salt has a chiral center)) that, when administered to a mammal for treating or preventing a state, disorder or condition is sufficient to effect such treatment or prevention. The "effective amount" will vary depending on the active ingredient, the state, disorder, or condition to be treated and its severity, and the age, weight, physical condition and responsiveness of the mammal to be treated. According to one embodiment of the present invention, a therapeutically effective amount of a compound is an amount effective to treat any one of the above mentioned disorders. The compound or its salt or salts may be augmented with a second medication (such as a chemotherapeutic agent, or adjunctive chemotherapeutic agent to treat any of the aforementioned disorders, such as malignancies).

An "effective amount of the pharmaceutical formulation" is an amount of the pharmaceutical formulation described which is effective to treat or prevent a condition in a subject to whom it is administered over some period of time, e.g., provides a therapeutic effect during a desired dosing interval. Generally, an effective amount of the pharmaceutical formulation includes amounts of compound its salt or salts to treat or prevent the desired condition over a desired period of time.

As used herein, the term "treat" includes one or more of the following:

(a) arresting, delaying the onset (i.e., the period prior to clinical manifestation of a disorder) and/or reducing the risk of developing or worsening a disorder;

(b) relieving or alleviating at least one symptom of a disorder in a mammal, including for example, cancer; or (c) relieving or alleviating the intensity and/or duration of a manifestation of a disorder experienced by a mammal including, but not limited to, those which are in response to a given stimulus (e.g., pressure, tissue injury or cold temperature).

The term "treat" also includes prophylactically preventing, curing, healing, alleviating, relieving, altering, remedying, ameliorating, improving, or affecting a condition (e.g., a disease), the symptoms of the condition, or the predisposition toward the condition.

The term "sustained release" as used herein refers to the release of an active ingredient over an extended period of time leading to lower peak plasma concentrations and a prolonged $T_{max}$ as compared to "immediate release" formulations of the same active ingredient.

The term "bioavailability" refers to the rate and extent to which the active ingredient (compound its salt or salts) or active moiety is absorbed from a drug product and becomes systematically available.

The term "polymorph" refers to crystallographically distinct forms of a substance.

The term "hydrate" as used herein includes, but is not limited to, (i) a substance containing water combined in the molecular form and (ii) a crystalline substance containing one or more molecules of water of crystallization or a crystalline material containing free water.

The term "solvate" as used herein includes, but is not limited to, a molecular or ionic complex of molecules or ions of a solvent with molecules or ions of a compound or its salt or salts.

The term "adjunctive chemotherapeutic agent" includes agents which treat, alleviate, relieve, or amelliorate the side effects of chemotherapeutic agents. Such agents include those which modify blood cell growth and maturation. Examples of adjunctive chemotherapeutic agents include, but are not limited to, filgrastim and erythropoietin.

The term "salt" includes compound salt or salts, complexes and active metabolites, prodrugs, racemates, enantiomers, and hydrates thereof.

The term "chemotherapeutic agent" includes any agent which treats, prevents, cures, heals, alleviates, relieves, alters, remedies, ameliorates, improves, or affects malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, docetaxel, doxorubicin, flutamide, interferon-alpha, letrozole, leuprolide, megestrol, mitomycin, paclitaxel, plicamycin (Mithracin™), tamoxifen, thiotepa, topotecan, valrubicin, vinylastin, vincristine, and any combination of any of the foregoing. Further examples are provided herein.

The term 'Hydrogen" or "H" includes any form of hydrogen, including deuterium.

Compounds

The present invention provides compounds and compositions which treat and prevent cancer. Compounds of the present invention include those having the following formula I:

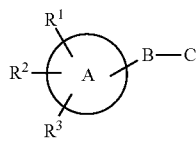

or a pharmaceutically acceptable salt or pharmaceutically acceptable derivative thereof, wherein:

Ring A is selected from the group consisting of one or more monocyclic aryl, one or more heteroaryl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen, or sulfur;

each $R^1$, $R^2$, and $R^3$ independently selected from the group consisting of hydrogen, halogen, deuterium, $CF_3$, CN, OR, SR, NRR, NRCOR, NRCONRR, $NRCO_2R$, COR, $CO_2R$, NOR, $NO_2$, CONRR, OC(O)NRR, $SO_2R$, $SO_2NRR$, $NRSO_2R$, $NRSO_2NRR$, C(O)C(O)R, or $C(O)CH_2C(O)R$, alkyl, aryl, heteroaryl and morpholino, wherein either $R^1$ and $R^2$, or $R^2$ and $R^3$ are optionally taken together to form a 4-8 membered saturated, partially unsaturated, or fully unsaturated ring having 0-3 heteroatoms independently selected from nitrogen, oxygen, or sulfur;

each R is independently selected from hydrogen or an optionally substituted $C_1$-$C_4$ aliphatic moiety (i.e. alkyl, alkenyl, or alkynyl), wherein:

or alternatively, two R moieties bound to the same nitrogen atom are optionally taken together with the nitrogen atom to form a 3-7 membered saturated, partially unsaturated, or fully unsaturated ring having 1-2 additional heteroatoms independently selected from nitrogen, oxygen, or sulfur;

B is selected from:

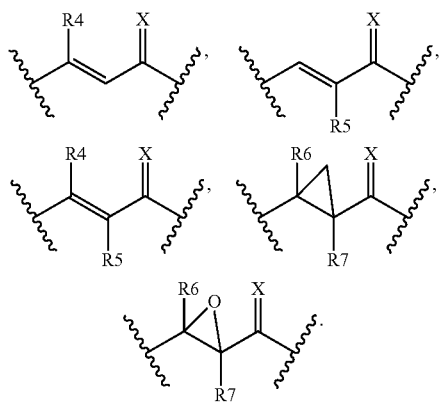

wherein

R4, R5, R6 and R7 are independently selected from a substituted or unsubstituted $C_1$ to $C_{12}$ alkyl, a substituted or unsubstituted $C_1$ to $C_{12}$ alkenyl or a substituted or unsubstituted $C_1$ to $C_{12}$ alkynyl;

X is O, S; and

C is a saturated or unsaturated heteroaryl or a saturated or unsaturated C1 to C7 heterocyclic containing one or more hetero atoms wherein the heteroatoms are independently selected from N, O or S;

or C is a fused ring; and wherein any one or more H is optionally replaced by a deuterium.

In another embodiment, the compounds of the invention are compounds of Formula I above wherein ring A is selected from:

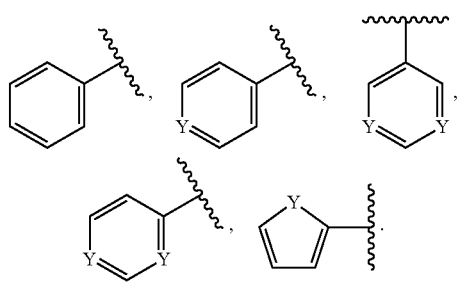

wherein the ring carries $R^1$, $R^2$ and $R^3$ as defined above;

wherein Y is N, O or S; and

C is selected from:

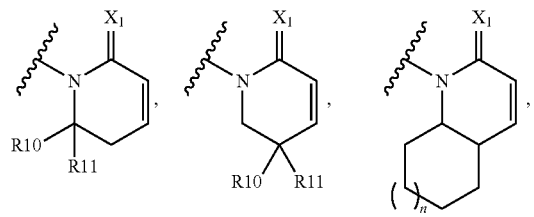

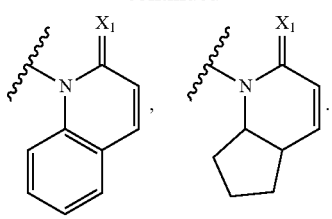 , 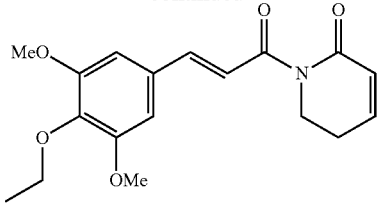 .

wherein the ring is optionally substituted with one or more $R^{10}$ and $R^{11}$, wherein $R^{10}$ and $R^{11}$ are independently selected from a substituted or unsubstituted $C_1$ to $C_{12}$ alkyl, a substituted or unsubstituted $C_1$ to $C_{12}$ alkenyl or a substituted or unsubstituted $C_1$ to $C_{12}$ alkynyl, an ether, a thioether, aryl, n is 1, 2 or 3;

$X_1$ is O or S;

In a preferred embodiment, the compound of formula I is represented by the following compounds:

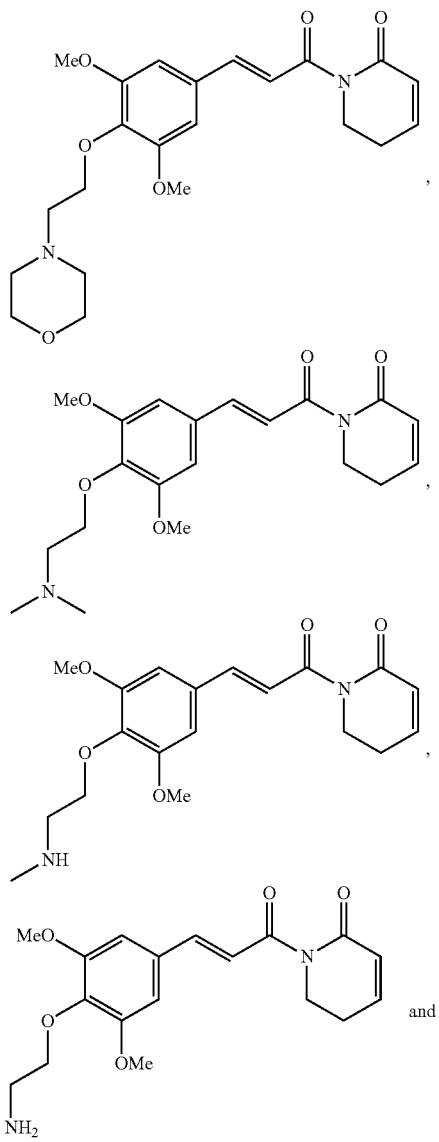

In one embodiment, the compounds of the present invention interact with proteins to increase ROS in cancer cells but not in normal cells. In one embodiment, the compounds of the present invention increase phosphor-JNK levels. In one embodiment, the compounds of the present invention increase p53 activity. In one embodiment, the compounds of the present invention increase p21 activity. In one embodiment, the compounds of the present invention decrease pro-survival gene activity. In one embodiment, the compounds of the present invention induce apoptosis in cancer cell lines.

In another embodiment, the one or more compounds of the instant invention are used to treat cancer. Another embodiment includes a method for increasing apoptosis by administering a compound of the instant invention. Another embodiment includes a method for increasing p53 activity by administering one or more compounds of the instant invention. Another embodiment includes a method for increasing p21 activity by administering one or more compounds of the instant invention. Another embodiment includes a method of preferentially inducing DNA damage in cancer cells by administering one or more compounds of the instant invention. Another embodiment is a method of suppressing DNA damage in normal cells by administering one or more compounds of the instant invention.

In another embodiment, the invention provides a method for improving the expression of proteins associated with normal cell survival. In another embodiment, the invention provides for a method of sparing normal cells while killing cancer cells.

In another embodiment, the invention provides a method of administering a compound of the instant invention at a dose of about 100 mg/kg to about 3000 mg/kg. In another embodiment the invention provides a method of administering a compound of the instant invention at a dose of about 2.5 mg/kg to about 10 mg/kg. In some embodiments, a therapeutically effective amount is less than 50 mg/kg, such as less than 45 mg/kg, less than 40 mg/kg, less than 35 mg/kg, less than 30 mg/kg, less than 25 mg/kg, less than 20 mg/kg or less than 15 mg/kg. In some embodiments, a therapeutically effective amount is less than 10 mg/kg, such as less than 9 mg/kg, less than 8 mg/kg, less than 7 mg/kg, less than 6 mg/kg, less than 5 mg/kg, less than 4 mg/kg, less than 3 mg/kg or less than 2 mg/kg. In some embodiments, a therapeutically effective amount is less than 1.5 mg/kg, such as less than 1.4 mg/kg, less than 1.3 mg/kg, less than 1.2 mg/kg, less than 1.1 mg/kg, less than 1 mg/kg, less than 0.9 mg/kg, less than 0.8 mg/kg, less than 0.7 mg/kg, less than 0.6 mg/kg, less than 0.5 mg/kg, less than 0.4 mg/kg, less than 0.3 mg/kg, less than 0.2 mg/kg or less than 0.1 mg/kg.

In another aspect, the invention provides a method for inhibiting cell proliferation. In some embodiments, the method for inhibiting cell proliferation comprises contacting a cell with an effective amount of a composition comprising a compound of the invention to inhibit the proliferation of the cell. In some embodiments, the method further comprises contacting the cells with a compound of the invention and a chemotherapeutic agent. In another aspect, the invention provides a method for increasing apoptosis of a cell or in a population of cells. In some embodiments, the method for increasing apoptosis of a cell or in a population of cells, the method comprises contacting the cell or population of cells with an effective amount of a composition comprising a compound of the invention to increase apoptosis in the cell or population of cells. In some embodiments, the number of apoptotic cells in a population of cells is increased by at least two-fold. In some embodiments, the number of apoptotic cells in a population of cells is increased by at least five-fold. In some embodiments, the number of apoptotic cells in a population of cells is increased by at least ten-fold. In some embodiments, the method further comprises contacting the cells with a compound of the invention and a chemotherapeutic agent.

In another embodiment one or more compounds of the instant invention are administered with one or more chemotherapeutic agent. In another embodiment, one or more compounds of the instant invention are administered prior to one or more chemotherapeutic agents. In another embodiment, one or more compounds of the instant invention are administered following one or more chemotherapeutic agents.

Chemotherapeutic agents include, but are not limited to an agent which is administered to a subject for the purpose of treating a cancer. Chemotherapeutic agents include, but are not limited to antiproliferative compounds, anti-neoplastic compounds, anti-cancer supplementary potentiating agents and radioactive agents. One of ordinary skill in the art is familiar with a variety of chemotherapeutic agents, or can find those agents in the routine art, which are used in the medical arts to treat cancer.

Chemotherapeutic agents include, but are not limited to, the following sub-classes of compounds: Antineoplastic agents such as: Acivicin; Aclarubicin; Acodazole Hydrochloride; Acronine; Adozelesin; Adriamycin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Buniodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorombucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Ifesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin 30 Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; 5 Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin, Mitosper; Mitotane; Mitoxantrone Hydrochloride; Mycophenolic Acid; Nocodazole; Nogalamycin; Ormaplatin; Oxisuran; Paclitaxel Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate, Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid, 2-chloro-2'-arabinofluoro-2'-deoxyadenosine; 2-chloro-2'-deoxyadenosine; anisomycin; trichostatin A; hPRL-G129R; CEP-751; linomide; Piritrexim Isethionate; Sitogluside; Tamsulosin Hydrochloride and Pentomone. Anti-neoplastic compounds include, but are not limited to 20-epi-1,25 dihydroxyvitamin D3; 5-ethynyluracil; abiraterone; aclarubicin; acylfulvene; adecypenol; adozelesin; aldesleukin; ALL-TK antogonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; 15 cis-porphyrin; cladribine; clomifene analogues; clotrimazole; collismycin A; collismycin 13; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin 10 deslorelin; dexifosfamide; dexrazoxane; dexverapamil;

diaziquone; didemnin B; didox; diethylnorspermine; dihydro-5-azacytidine; dihydrotaxol; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones; epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistancegene inhibitor, multiple tumor suppressor 1-based therapy; mustard anticancer agent; 15 mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; Sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; 5 sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer. Anti-cancer supplementary potentiating agents include, but are not limited to, Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca_{2+}$ antagonists (e.g., verapamil, nifedipine, nitrendipine and caroverine); Calmodulin inhibitor (e.g. prenylamine, trifluoroperazine and clomipramine); Amphotericin B; Triparanol analogues (e.g. tamoxifen); anti-arrhythmic drugs (e.g., quinidine); antihypertensive drugs (e.g. reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Radioactive agents include but are not limited to Fibrinogen I 125; Fludeoxyglucose F18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate-23-Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate-Hg 203; Merisoprol Hg 197; Selenomethionine Se 75; Technetium Tc 99m Atimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium 99m Lidofenin; Technetium Tc 99 mm Mebrofenin; Technetium Tc 99m Medronate; TechnetiumTc 99m Medronate Disodium; Technetium Tc 99m Mertiatide; Technetium Tc 99m Oxidronate; Technetium Tc 99m Pentetate; Technetium Ic 99m Pentetate Calcium Trisodium; Technetium Tc 99m Sestamibi; Technetium Tc 99m Siboroxime; Technetium Tc 99m Succimer; Technetium Tc 99m Sulfur Colloid;

Technetium Tc 99m Teboroxime; Technetium Tc 99m Tetrofosmin; Technetium Tc 99m Tiatide; Thyroxine I 125: Thyroxine I 131; Tolpovidone I 131; Triolein I 125; Triolein I 131.

The compounds of the instant invention are efficacious in the treatment and/or prevention of a broad range of cancers. Such cancers include but are not limited to lung cancer, bladder cancer, melanoma, bladder carcinoma, pancreatic cancer, breast cancer.

In one aspect, the invention provides methods for the treatment of cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma or hematopoietic cancer. Cancer, as used herein, includes the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

The compounds may be in the form of the carboxylic acid and/or their salts. Salts include but are not limited to organic and inorganic salts, for example alkali-metal salts, such as sodium, potassium and lithium; alkaline-earth metal salts, such as magnesium, calcium or barium; ammonium salts; basic amino acids such as lysine or arginine; and organic amines, such as dimethylamine or pyridine. Preferably, the salts are tartrate and will be hydrochloride salts. The salts may be mono- or multi-valent salts, such as monosodium salts and di-sodium salts. The salts may also be solvates including ethanol solvates.

The compounds described herein can be readily prepared synthetically by methods described herein. For example, the compounds may be prepared as in Example 1. Other methods of preparation are known to those skilled in the art and are found, for example in Synthesis of diverse analogues of Oenostacin and their antibacterial activities (Vandana, Bioorganic & Medicinal Chemistry 15 (2007) 518-525); A Simple Regioselective Demethylation of p-Aryl Methyl Ethers Using Aluminum Chloride-Dichloromethane System (Negi, Synthetic Communications, 35: 15-21, 2005); Antiplatelet Activities of Newly Synthesized Derivatives of Piperlongumine (Park, *Phytother. Res.* 22, 1195-1199 (2008)); On the structure of Pipertine and a synthesis of dihydropiplartine (Joshi, Tetrahedron Letters No. 20, pp. 2395-2420, 1968); Synthesis and Molecular Structure of Piplartine (Boll, Tetrahedron Letters No. 40, pp. 171-175, 1984); Isolation, Synthesis and Evolutionary Ecology of *Piper* Amides: June 2004 (Dyer); Inter- and Intraspecific Compararisons of Antiherbivore Defenses in Three Species of Rainforest Understory Shrubs (Fincher, J Chem Ecol (2008) 34: 558-557). The contents of these references and these methods are incorporated by reference in their entirety.

Salts of the present compound may be made by methods known in the art. For example, sodium salts may be made by dissolving the compound in ethanol and adding aqueous sodium hydroxide. Hydrochloride and Tartrate salts are prepared as described in Examples 1 and 2.

Scheme I represents the preparation of Compound 1 and its tartaric acid salt.

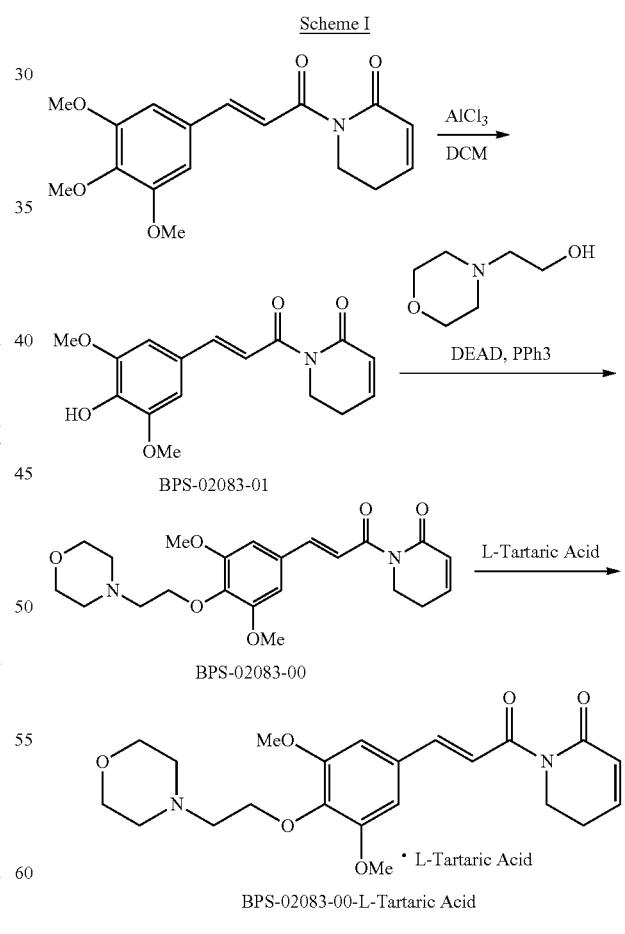

Another embodiment is a method of preparation of the compounds of the instant invention. In yet another embodiment, the preparation of the representative compounds of the instant invention is represented by Scheme II:

Scheme II-Preparation of representative compounds of the invention.

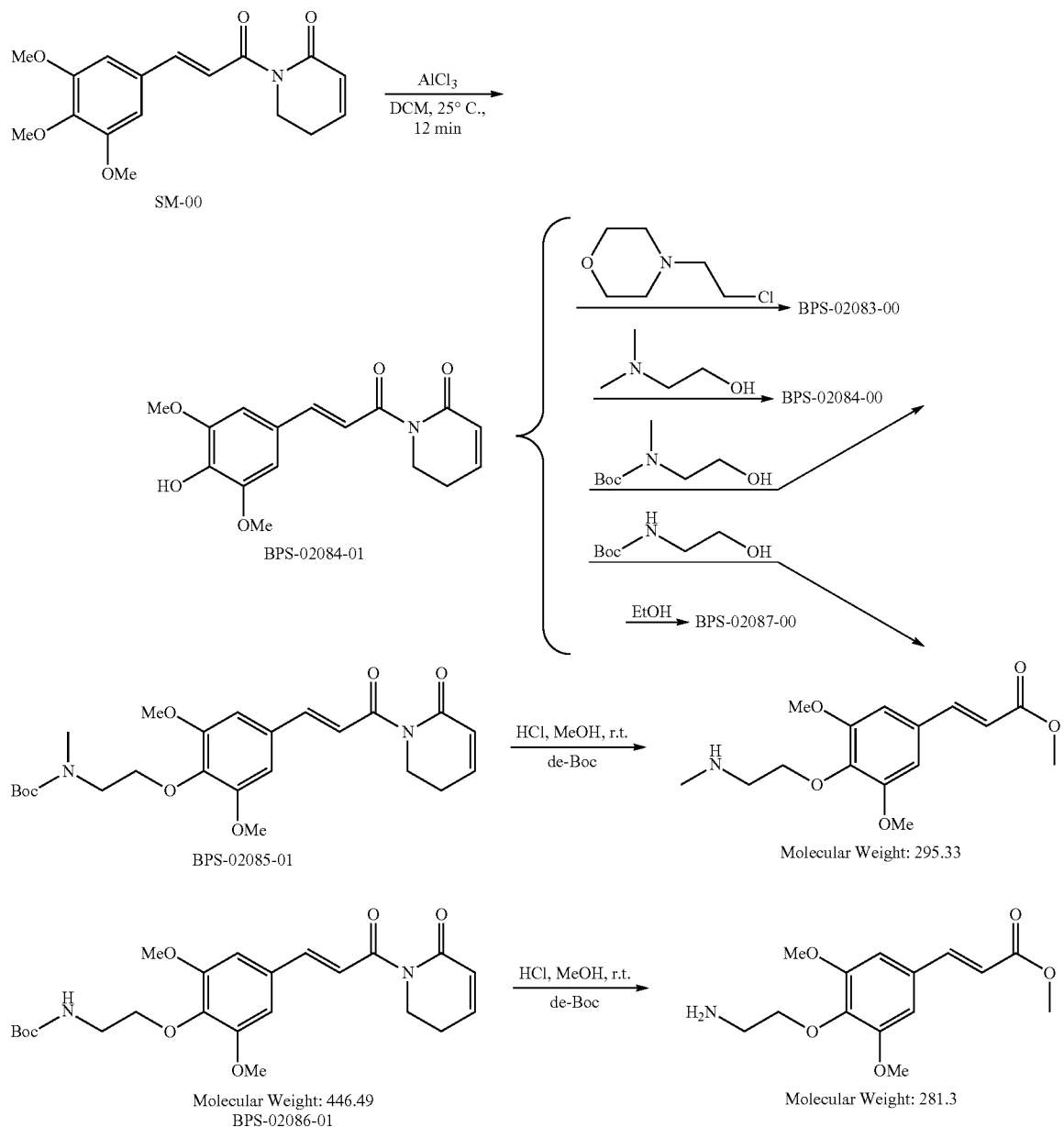

Mechanism

Without being bound to any particular theory, the compounds of the present invention exert their therapeutic effect by reducing oxidative stress and thereby reducing damage to DNA in normal cells while increasing ROS levels in cancer cells. The resulting effect of exposure to Reactive oxygen species (ROS) is often changes in cell differentiation and finally, over a prolonged period, apoptosis. Under non-stressed conditions, GSTP1 inhibits JNK phosphorylation by sequestering the JNK-c-JUN complex. Stressor triggers oligomeraization of GSTP1 and results in dissociation of the JNK-c-JUN complex. JNK can then become phosphorylated and activate downstream kinase and transcription factors.

Reactive oxygen species (ROS) have been shown to be increased in, for example, EJ Bladder Carcinoma cells, Breast Carcinoma cells, and removal of GSTJI has been shown to block the increase in ROS. SP2007 has been shown to increase ROS in cancer cells and causes apoptosis. Other compounds of this invention have been shown to be efficacious in vivo against pancreatic cancer cells, breast epithelium and EJ Bladder cancer cells.

Furthermore, compounds of the instant invention are superior to the traditional *Piper longum* parent molecule in that the compounds are highly soluble. For example whereas the parent *Piper longum* can dissolve only in quantities of 0.1 mg/ml in water, much larger quantities of compounds of the present invention are soluble in water. For example, the tartrate salt of compound one of the present invention is soluble at 100 mg/ml of water.

Pharmaceutical Forms

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze drying, precipitation, crystallization and solid dispersion.

The amount of compound used in an administration composition of the present invention is an amount effective to accomplish the purpose of the particular compound. However, the amount can be less than that amount when the composition is used in a dosage unit form because the dosage unit form may contain a plurality of compound compositions or may contain a divided pharmacologically, biologically, therapeutically, or chemically effective amount. The total effective amount can then be administered in cumulative units containing, in total, an effective amount of the active agent.

The total amount of compound to be used can be determined by methods known to those skilled in the art.

The presently disclosed compounds may be in any dosage form known to those skilled in the art, particularly suitable for oral, intranasal, sublingual, intraduodenal, subcutaneous, buccal, intracolonic, rectal, vaginal, mucosal, pulmonary, transdermal, intradermal, parenteral, intravenous, intramuscular, intrathecal, intraperitoneal and ocular administrations, as well as traversing the blood-brain barrier. The compounds may also be prepared for injections, either by infusion into a vein or artery or injected into the peritoneum, bladder, or directly into tumors. Topical preparations such as creams, ointments, gels, lotions or transdermal patches are contemplated dosage forms.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The compounds of the invention can be administered to animal and man, directly or together with a vehicle commonly used. The dose form is not particularly limited, and is selected appropriately as needed on use, including oral drugs such as tablets, capsules, granules, grains and powder, or non-oral drugs such as injection and suppository.

The oral drugs are prepared by ordinary methods, using starch, lactose, sucrose, mannitol, carboxymethylcellulose, corn starch, or inorganic salts.

In the drugs of this type, use can be made of a binder, a disintegrator, a surfactant, a lubricant, a fluidity-promoting agent, a flavor, a tinction, a perfume and the like, in addition to the vehicle mentioned above. Non-limiting examples of some of these substances are presented below:

Binder: Starch, dextrin, powdered acasia, gelatin, hydroxypropylstarch, methylcellulose, carboxymethylcellulose sodium, hydroxypropylcellulose, crystalline cellulose, ethylcellulose, polyvinylpyrrolidone, and macrogol.

Disintegrator: Starch, hydroxypropylstarch, carboxymethylcellulose sodium, carboxymethylcellulose calcium, carboxymethylcellulose, and low-substituted hydroxypropylcellulose.

Surfactant: Sodium laurylsulfate, soybean lecithin, succharose fatty acid ester, and polysorbate 80.

Lubricant: Talc, waxes, hydrogenated vegetable oil, succharose fatty acid ester, magnesium stearate, calcium stearate, aluminum stearate, and polyethylene glycol.

Fluidity-Promoting Agent: Light anhydrous silicic acid, dry aluminum hydroxide gel, synthetic aluminum silicate, and magnesium silicate.

The compounds of the present invention can also be administered in the form of suspension, emulsion, syrup or elixir. These forms of drugs may also contain flavor, perfume and tinction.

The non-oral drugs can be prepared by ordinary methods, and use may be made of an attenuant such as distilled water for injection, physiological saline, aqueous solution of glucose, vegetable oil for injection, sesame oil, peanut oil, soybean oil, corn oil, propylene glycol, or polyethylene glycol. If necessary, germicide, preservative, and stabilizer may be added. The non-oral drugs can be filled in a vial or the like and frozen, and then be removed of water by the ordinary freeze-dry technique. A liquid drug can be reformulated from the freeze-dried drug immediately before administration. Further, an isotonic, a stabilizer, a preservative, an antiseptic, a sedative, and the like may be added.

The compositions comprising the compounds have utility in the treatment of cancer.

DESCRIPTION OF THE PREFERRED EMBODIMENTS

The following examples illustrate the invention without limitation. All parts are given by weight unless otherwise indicated.

EXAMPLE 1

Compound Preparation

1a. Preparation of Compound 1 and its Tartaric Acid Salt.

Scheme I represents the preparation of Compound 1 and its tartaric acid salt.

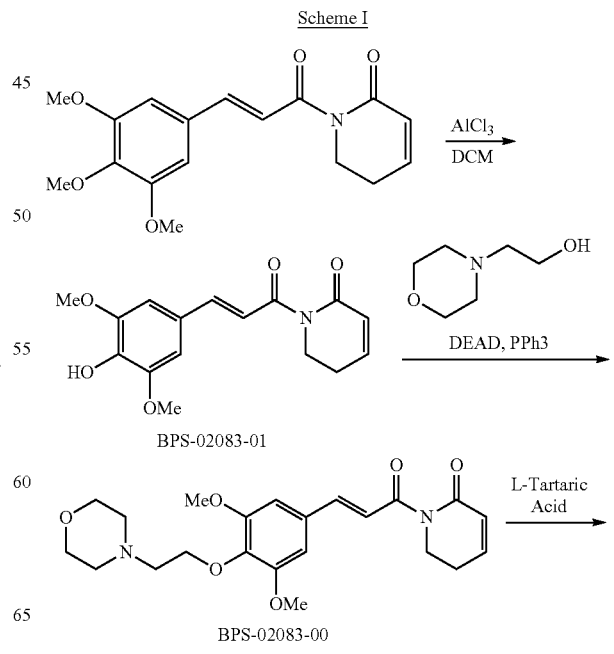

-continued

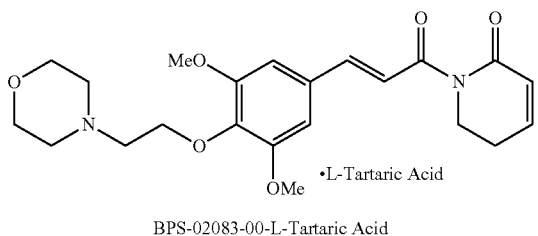

BPS-02083-00-L-Tartaric Acid

Preparation of BPS-02083-01

To a stirred solution of Piperlongumine (5.60 g, 17.6 mmol) in anhydrous DCM was added AlCl3 (23.3 g, 174 mmol) at 28° C. AlCl$_3$ cannot be completely dissolved in the solution and the red suspension became a yellow suspension while stirred at 28° C. for 15 min. Saturated NaHCO31 was added and the mixture was extracted with dichloromethane (150 mL*2). The combined organic layers were washed with brine (50 mL*3), dried over anhydrous Na2SO4, concentrated in vacuo and washed with dichloromethane/petroleum ether (v/v=2:3) to give BPS-02083-01 (3.5 g, 11.6 mmol, 66%) as a yellow solid. MS (ESI/FT-MS): 304 [M+H]$^+$; expected 304.

Preparation of Compound I

To a stirred solution of BPS-02083-01 intermediate (1.94 g, 6.4 mmol), 2-morpholinoethanol (1.0 g, 7.7 mmol) and PPh3 (2.52 g, 9.6 mmol) in anhydrous dichloromethane (80 mL) was added slowly a solution of DEAD (1.67 g, 9.6 mmol) in dichloromethane (20 mL) under N2 at 0° C. The mixture was slowly warmed to room temperature and stirred overnight. The solvent was removed in vacuo and purified by chromatography on silica gel (petroleum ether/ethyl acetate=1:1 to 2:1) to give BPS-02083-00 (1.4 g, 3.37 mmol, 53%) as a pale yellow oil. MS (ESI/FT-MS): 417 [M+H]$^+$; expected 417.

Compound 1-L-tartaric acid salt.

To a solution of BPS-02083-00 [Compound 1] (4.16 g, 10.0 mmol) in dichloromethane (25 mL) was added a solution of L-tartaric acid (1.50 g, 10.0 mmol) in dichloromethane/ methanol (10 mL). The solvent was removed in vacuo to give the L-tartaric acid salt of BPS-02083-00 (5.66 g, 10.0 mmol, 100%) as a colorless solid. MS (ESI/FT-MS): 417 [M+H]$^+$; expected 417, same as the free base.

EXAMPLE 2

Attempted Preparation of Compound I HCL Salt 5 gram free base of Compound I (thick oil) (~97% by HPLC). BPS-02083-00 (100 mg) was dissolved in ether (2.0 mL) and cooled to −10° C. HCl in ether (saturated) was added and stirred for 10 min. The solvent was removed (<25° C.) to give a colorless solid (BPS-02083-00-HCl). The spectra indicated that it is not the HCl salt of BPS-02083-00. The structure is B (HCl addition to double bond).

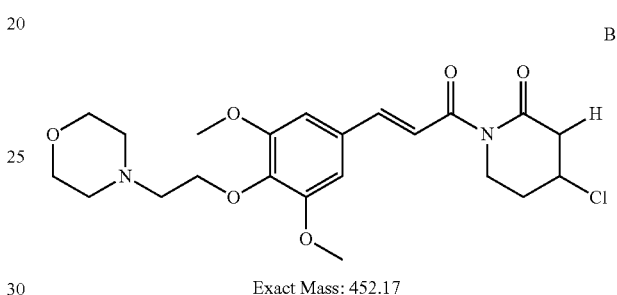

Exact Mass: 452.17

EXAMPLE 3

Preparation of Representative Compounds of the Invention

The Intermediate was prepared as in Example 1 and the procedure for the de-boc step to form the by product is as follows. To a solution of BPS-02085 (about 35 mg) in menthol (5.0 ml) was bubled HCl(g) for 15 minutes at room temperature (20° C.). The solvent was removed in vacuo and the residue was purified by TLC (DCM:MA:NH3H2O=70: 4:1) to give by-product (confirmed by 1NMR and LCMS). Non-limiting example of compounds which may be prepared by the ad-boc method described in Example 3 are represented below.

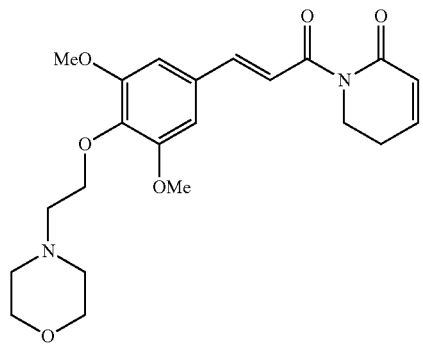

BPS-02083-00

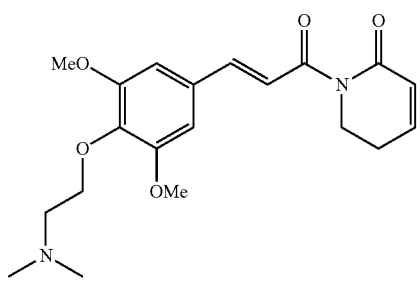

BPS-02084-00

-continued
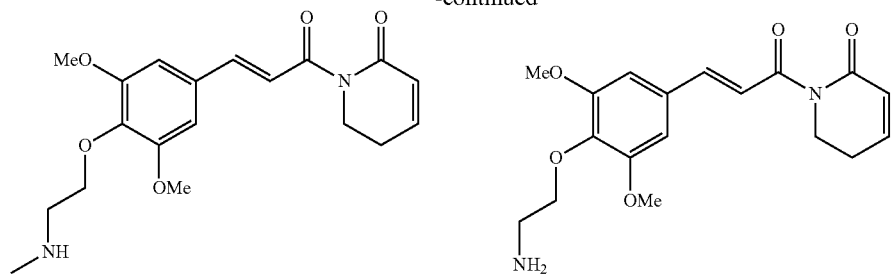
BPS-02085-00
BPS-02086-00
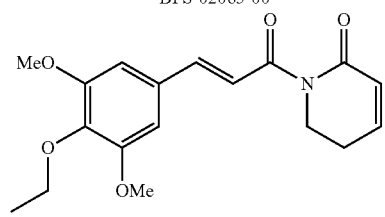
BPS-02087-00
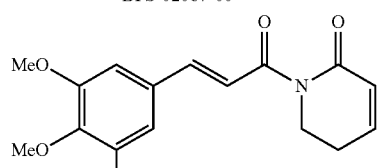
SM-00
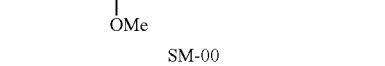
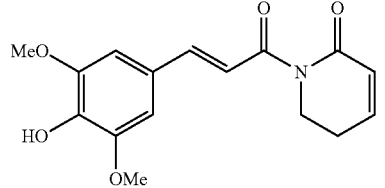
BPS-02084-01
68% yield
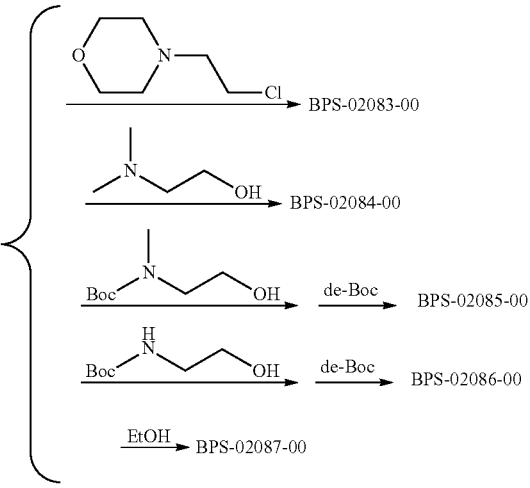
EXAMPLE 4
Report of Representative Compounds
| SM | Quantity | Product | Quantity | HPLC | HNMR | LCMS[M + H]+ |
|---|---|---|---|---|---|---|
| SM-00 | 190 mg | BPS-02084-01 | 124 mg + 32 mg SM-00 | >95% | Passed | 304 |
| SM-00 | 9.3 mg | BPS-02084-01 | 254 mg + 84 mg SM-00 | >95% | Passed | 304 |
| SM-00 | 13 mg | | | | | 304 |
| SM-00 | 176 mg | | | | | 304 |
| SM-00 | 190 mg | | | | | 304 |
| BPS-02084-01 | 56 mg | BPS-02083-00 | 7.1 mg | 95.0% | Passed | 417 |

EXAMPLE 5

Effect of Compound on Pro-Survival Gene Suppression

Additional studies will demonstrate that compounds of the instant invention have a large therapeutic window by sparing normal cells, such as fibroblasts and keratocytes, but killing tumors cells, such as EJ cells and HCT116 cells. Studies will also demonstrate that DNA in normal cells remains unaffected by compounds of the instant invention and that there is no increase in ROS in normal cells.

FIGS. 1-4 show in-vivo efficacy of the compounds against pancreatic cancers cells, breast epithelium and EJ Bladder Cancer Cells.

EXAMPLE 6

Antitumor Effect of SP2007 and SP83 on Bladder Tumor Xenograft-Bearing Mice

We tested the anti-tumor effect SP2007 and SP83 in bladder tumor xenograft-bearing mice.

Figure 5:
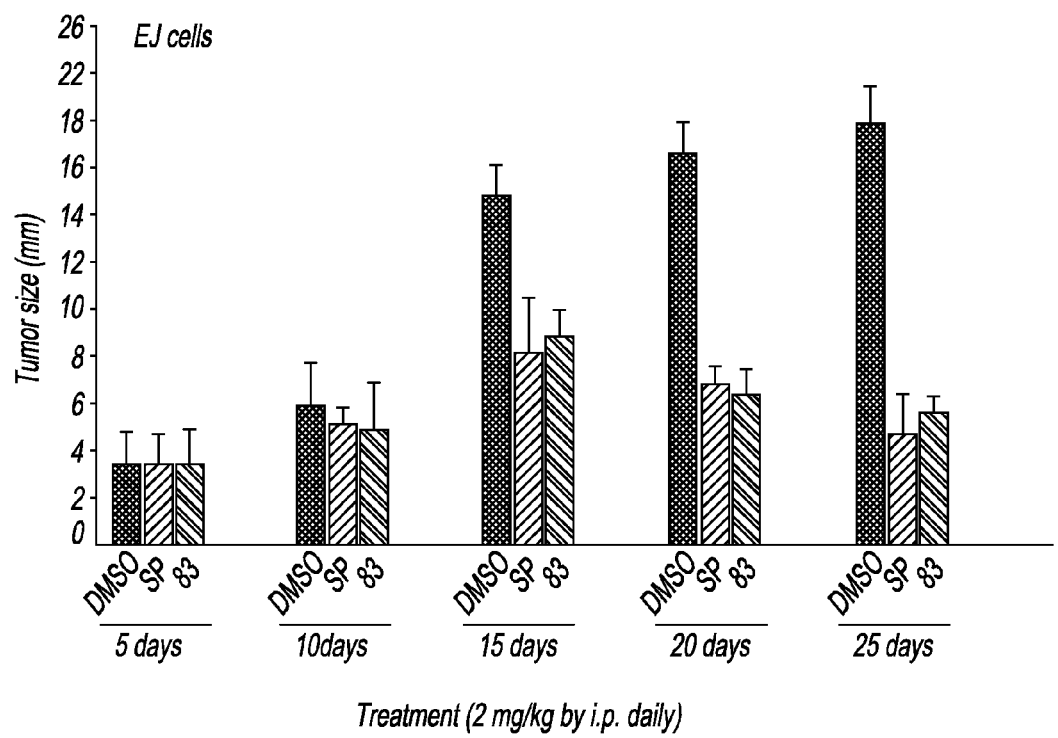
FIG. 5 shows the effect of SP2007 and SP83 on bladder tumor xenograft-bearing mice
Figure 6:
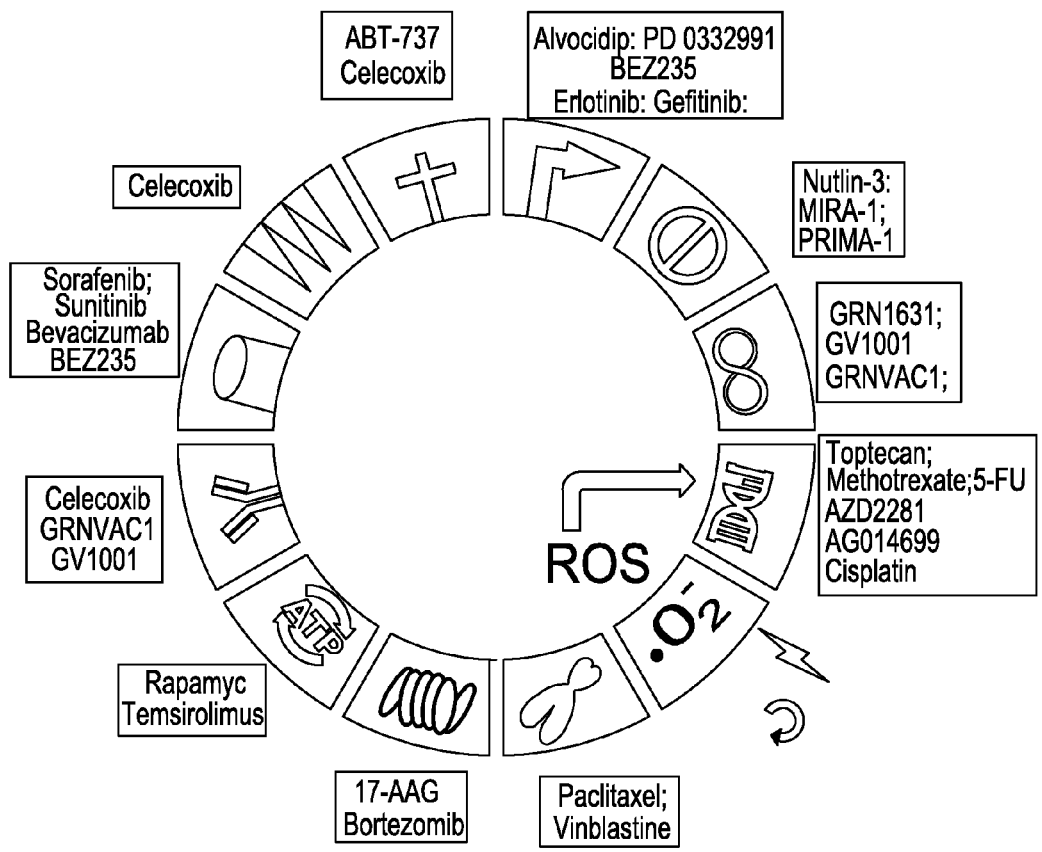
FIG. 6 shows cancer therapies targeting various hallmarks of cancer.

Four nude/nude mice weighing approximately 0.02 Kg were fasted overnight and anestatized with Avertin (2,2,2, Tribromoethanol), 250 mg/kg, body weight; 1P injection. A total 2×106 EJ cells (acquired from Japanese cellbank) were implanted subcutaneously on opposite site flanks in each of four nude/nude mice in each treatment group. Mice were fed and given water ad lib. When tumor masses grew to approximately 2 to 5 mm in diameter, control vehicle, SP2007 or SP83 were administered intraperitoneally (total 2 mg/kg) every 24 hours for 25 days. Anti-tumor effects were observed in SP2007 and SP83 administered tumor mice, as compared to control DMSO-administered tumor mice. Results are shown in FIG. 5.

Although this invention has been described with a certain degree of particularity, it is to be understood that the present disclosure has been made only by way of illustration and that numerous changes in the details of construction and arrangement of parts may be resorted to without departing from the spirit and the scope of the invention. Many variations of the present invention will suggest themselves to those skilled in the art in light of the above detailed description. All such obvious variations are within the fully intended scope of the appended claims.

What is claimed is:

1. A compound or a pharmaceutically acceptable salt thereof, wherein the compound is selected from:

Report of Representative Compounds

| SM | Quantity | Product | Quantity | HPLC | HNMR | LCMS[M + H]+ |
|---|---|---|---|---|---|---|
| BPS-02084-01 | 56 mg | BPS-02084-00 | 22 mg | 96.1% | Passed | 375 |
| BPS-02084-01 | 96 mg | BPS-02085-01 | 30-40 mg | >90% | | Passed |
| BPS-02085-01 | 30-40 mg | BPS-02085-00 | 0 mg | | | |
| BPS-02084-01 | 65 mg + 36 mg | BPS-02086-01 | 25-30 mg | >90% | | Passed |
| BPS-02086-01 | 25-30 mg | BPS-02085-00 | 0 mg | | | |
| BPS-02084-01 | 56 mg | BPS-02087-00 | 42 mg | 97.1% | Passed | 332 |

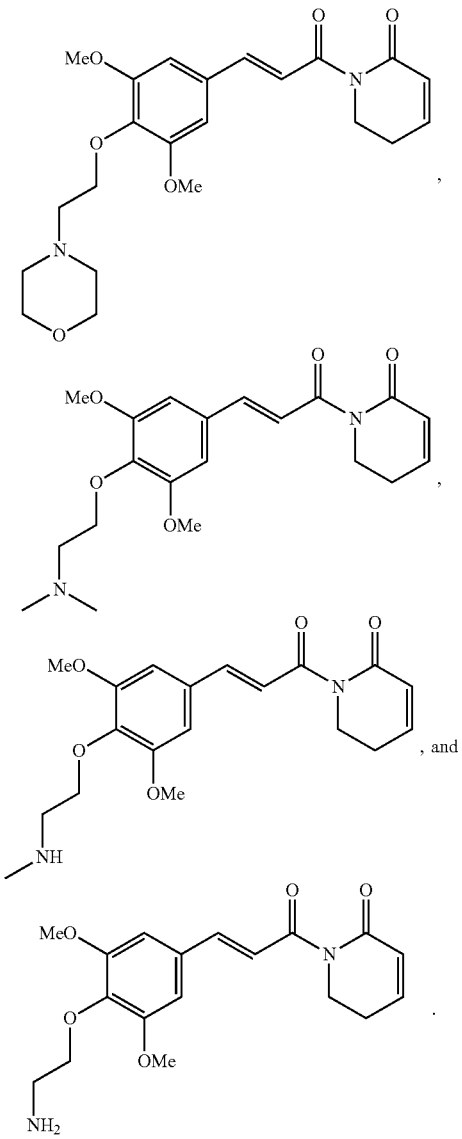

2. A pharmaceutical composition comprising one or more compounds of claim 1 or a pharmaceutically acceptable salt thereof, and a pharmaceutically acceptable carrier.

3. The pharmaceutical composition of claim 2, further comprising one or more chemotherapeutic agents.

4. A kit comprising a pharmaceutical composition comprising a compound of claim 1 or a pharmaceutically acceptable salt thereof, and instructions for preparation and/or administration of the pharmaceutical composition.

5. The kit of claim 4, further comprising one or more chemotherapeutic agents.

6. A method for, delaying an onset of, reducing a risk of developing or worsening of, relieving or alleviating a symptom of, or relieving or alleviating an intensity or duration of a manifestation of a cancer in a subject, the method comprising: administering to a subject in need thereof a compound of claim 1 or a pharmaceutically acceptable salt thereof, wherein the cancer is selected from the group consisting of a pancreatic cancer, a breast cancer, and a bladder cancer.

7. The method of claim 6, comprising inhibiting further growth of the cancer, wherein the cancer is selected from the group consisting of a pancreatic cancer, a breast cancer, and a bladder cancer.

8. The method of claim 6 comprising administering to the subject from about 2.5 mg/kg to about 100 mg/kg of a compound of claim 3, or a pharmaceutically acceptable salt thereof.

9. A method for inhibiting cell proliferation, the method comprising: contacting a cell with a composition comprising a compound of claim 1, or a pharmaceutically acceptable salt thereof, to inhibit the proliferation of the cell, wherein the cell is selected from the group consisting of a pancreatic cancer cell, a breast cancer cell, and a bladder cancer cell.

10. A method for increasing apoptosis of a cell or in a population of cells, the method comprising: contacting the cell or population of cells with a composition comprising a compound of claim 1, or a pharmaceutically acceptable salt thereof, to increase apoptosis in the cell or population of cells, wherein the cell or population of cells is selected from the group consisting of a pancreatic cancer cell, a population of pancreatic cancer cells, a breast cancer cell, a population of breast cancer cells, a bladder cancer cell, and a population of bladder cancer cells.

11. A method for increasing p53 activity in a cell or population of cells, the method comprising: contacting the cell or population of cells with a composition comprising a compound of claim 1, or a pharmaceutically acceptable salt thereof, to increase p53 activity in the cell or population of cells.

12. The compound of claim 1, wherein said pharmaceutically acceptable salt is selected from tartrate and hydrochloride.

* * * * *

UNITED STATES PATENT AND TRADEMARK OFFICE
CERTIFICATE OF CORRECTION

PATENT NO. : 8,349,832 B2  
APPLICATION NO. : 12/874306  
DATED : January 8, 2013  
INVENTOR(S) : Michael Andrew Foley Page 1 of 1

It is certified that error appears in the above-identified patent and that said Letters Patent is hereby corrected as shown below:

Title Page, Col 1, Line 4, Item [75] (Inventors) delete "(US)" and insert -- (US); Sam Lee, Newton, MA (US) --, therefor.

Title Page, Col. 2, Line 3, Item (56) (Other Publications), delete "Hematalogy" and insert -- Hematology --, therefor.

Title Page, Col. 2, Line 15, Item (56) (Other Publications), delete "Dipydropiplartine," and insert -- Dihydropiplartine, --, therefor.

Title Page, Col. 2, Line 18, Item (56) (Other Publications), delete "Phythother." and insert -- Phytother. --, therefor.

Title Page, Col. 2, Line 23, Item (56) (Other Publications), delete "Dicholoromethane" and insert -- Dichloromethane --, therefor.

Col. 25, Line 22, In Claim 8, delete "claim 3," and insert -- claim 1, --, therefor.

Signed and Sealed this  
Ninth Day of April, 2013

Teresa Stanek Rea  
*Acting Director of the United States Patent and Trademark Office*